United States Patent [19]
Murakoshi et al.

[11] Patent Number: 4,810,872
[45] Date of Patent: Mar. 7, 1989

[54] OPTICAL PROPERTY MEASURING DEVICE

[75] Inventors: Takeo Murakoshi, Katsuta; Sadao Minakawa, Mito, both of Japan

[73] Assignee: Hitachi, Ltd., Tokyo, Japan

[21] Appl. No.: 76,292

[22] Filed: Jul. 22, 1987

[30] Foreign Application Priority Data

Jul. 26, 1986 [JP] Japan .................. 61-176466

[51] Int. Cl.⁴ .......................... G02F 1/01; G01J 3/50
[52] U.S. Cl. .................... 250/225; 250/226; 356/448; 356/432
[58] Field of Search ............ 356/448, 369, 367, 366, 356/432, 433, 438, 440, 446; 250/226, 225, 560

[56] References Cited

U.S. PATENT DOCUMENTS

| | | | |
|---|---|---|---|
| 2,146,904 | 2/1939 | McFarlane et al. | 356/443 |
| 3,746,869 | 7/1973 | Lindstedt et al. | 356/443 |
| 4,040,750 | 8/1977 | Zwiener | 356/448 |
| 4,555,181 | 11/1985 | Klumper et al. | 356/448 |
| 4,589,776 | 5/1986 | Carver et al. | 356/367 |
| 4,591,271 | 5/1986 | Byers | 356/432 |
| 4,672,196 | 6/1987 | Canino | 250/560 |

FOREIGN PATENT DOCUMENTS 0211327 10/1985 Japan .................. 356/448

Primary Examiner—David C. Nelms
Assistant Examiner—Michael Messinger
Attorney, Agent, or Firm—Antonelli, Terry & Wands

[57] ABSTRACT

Light irradiated to a sample is detected by a detector in order to measure the optical properties of the sample. The image of a minute virtual light source for the light is focused in the neighborhood of the measuring face of the sample by a first optical system arranged between the light source and the sample. The light outgoing from the sample is incident to the detector by way of a second optical system arranged between the sample and the detector and having conjugate points in the neighborhood of the measuring face of the sample and of the light receiving point of the detector.

9 Claims, 6 Drawing Sheets

OPTICAL PROPERTY MEASURING DEVICE

BACKGROUND OF THE INVENTION

This invention relates to an optical property measuring device and more particularly to an optical property measuring device for measuring the reflectance and transmittance of a sample to be measured such as a small-sized or minute beam splitter prism.

The beam splitter prism is an important optical element for use in, e.g. the sound recording, image recording and playback of a laser disk. This beam splitter prism, as shown in FIGS. 3 and 4, is shaped in a cube formed by bonding two 45° prisms to each other or its modification and has a bonding face subjected to particular treatment so that incident light is separated into transmission light and reflecting light with a certain ratio. Incidentally, in FIGS. 3 and 4, 1 denotes the bonding face, and I, T and R denote incident light, transmission light and reflection light, respectively.

One method of measuring the reflectance of a certain plane in order to manage the optical property mentioned above is to use an optical system for absolute reflectance measurement, as disclosed in, e.g., HATSUMEI KYOKAI KOKAI GIHO No. 79-1150. This method, when a sample to be measured takes the form of a cube such as shown in FIGS. 3 and 4 and is minute in its size, requires a complicated mechanism and sophisticated managing technique in order to hold the optical system so that the incident light flux is correctly incident to the central portion of the sample and also the reflection plane (bonding face in the present case) is directed in a normal direction.

For example, when using the above measuring method, in order to measure a beam splitter prism having a very small size of about 3 mm$^3$, the projected light flux should have a very small diameter of about 1.5 mm$\phi$. Further, if a sample holder, i.e., means for holding the beam splitter prism should be arranged in a normal direction with an inclination of up to 1/200° by arranging the beam splitter prism at a normal position with an error of about 0.2 mm. Otherwise, the reflection light comes out of the light receiving face of the integrating-sphere, thus providing some measuring error. On the other hand, the bonding face of the beam splitter prism, as seen from the perspective view of FIG. 5, may have a step displacement of 20$\mu$ or more because of the fabrication technique and of being not required as a product. If such a beam splitter prism is set in the planar sample holder, an inclination exceeding 1/200° necessarily occurs. Namely, even if the sample is slightly inclindely set in the holder, poor reproducibility results. This makes it impossible to measure the sample at a high speed and high accuracy, thus disadvantageously providing different measurement values for the same products or samples although the same holding method is used.

SUMMARY OF THE INVENTION

In view of the foregoing problems of the prior art, it is an object of this invention to provide an optical property measuring device which is capable of measuring the reflectance and transmittance of a sample such as a beam splitter prism, particularly a very small one at good reproducibility.

In order to attain the above object, in accordance with this invention, there is provided an optical property measuring device in which the light irradiated to a sample to be measured is detected by a detector to measure the optical properties of the sample, comprising a first optical system arranged between a minute virtual light source of the light and the sample, for focusing the image of the light source in the neighborhood of the measurement face of the sample and a second optical system arranged between the sample and the detector, having conjugate points in the neighborhood of the measurement face of the sample and of the light receiving portion of the detector.

DESCRIPTION OF THE PREFERRED EMBODIMENTS

The arrangement of this invention will be explained using an embodiment with reference to drawings.

Figure 1:
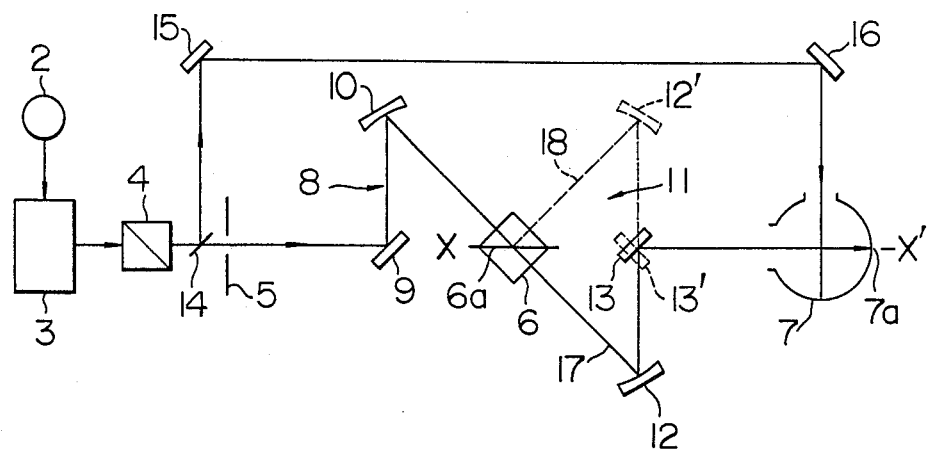
FIGS. 1 shows an optical arrangement of the optical property measuring device in accordance with one embodiment of this invention.

In FIG. 1, 2 is a light source, 3 is a spectroscope, 4 is a polariscope (polarizer), 5 is a diaphragm or slit, 6 is a sample to be measured; 7 is a detector; 8 generally designated is a first optical system consisting of a plane mirror 9 and e.g. a spherical mirror 10; and 11 generally designated is a second optical system consisting of, e.g., a spherical mirror 12 which is a first deflection optical system and a plane mirror 13 which is a second deflection optical system. The spherical mirror 12 is adapted to be shiftable to a position symmetrical with respect to the line X-X' connecting the bonding center 6a of the sample 6 and the light receiving point 7a of the detector 7. The plane mirror 13 is adapted to be rotatable to a position symmetrical with respect to the line X—X' 12' and 13' denote the positions of the spherical mirror and plane mirror after they are shifted or rotated, respectively. Plane mirrors 14, 15 and 16 constitute a compensation light path for compensating the errors of measurement values due to the variation of the luminance of the light source.

The diaphragm 5 is so arranged that the light from the light source 2 is focused, via the spherical mirror 10, substantially on the center 6a of the sample 6. The spherical mirror 12 is so arranged that a substantially conjugate relation exists between the center 6a of the sample 6 and the light receiving point 7a of the detector 7.

Monochromatic light outgoing by way of the spectroscope 3 from the light source 2 is derived as polarized light by the polarizer 4. The polarized light is incident to the diaphragm 5. The light limited by the opening of the diaphragm 5 is served as point source light (minute virtual light source) for the first optical system 8 which is arranged between the sample 6 and the diaphragm 5, and the image of the point source light is focused in the neighborhood of the bonding center 6a of the bonding portion of the beam splitter prism (sample) 6. The light flux 17 having transmitted the bonding face of the bonding portion or the light flux 18 having reflected therefrom is focused in the neighborhood of the light receiving point 7a of the detector 7. It should be noted that the polarizer 4 is provided for the reasons that the beam splitter prism as a sample is assumed to be a polarizing prism and also that even when the sample is a mere beam splitter prism, the arranging of the values obtained from the measurement using P (pressure) waves and S (shape) waves which are linear polarization permits the measurement at higher accuracy.

The transmittance is measured as follows. The first and the second deflection optical system of the second optical system 11 are arranged at the positions 12 and 13, respectively, without setting the sample 6. In this state, the amount of light incident to the detector 7 is measured and stored. Next, the sample 6 is set at a predetermined position and the amount of light incident to the detector 7 is measured. The value thus obtained is divided by the stored value. Thus, the influences of the transmittances of the plane mirror 9, the optical elements 10, 12 and the plane mirror 13 are eliminated to provide the transmittance of the sample 6.

The reflectance is measured as follows. This is carried out in the same manner as the measurement of the transmittance. First, the first and the second deflection optical system of the second optical system 11 are arranged at the positions 12 and 13, respectively, without setting the sample 6. In this state, the amount of light incident to the detector 7 is measured and stored. Next, the sample 6 is set at a predetermined position, and the first and the second deflection optical system are shifted to the positions 12' and 13' which are symmetrical to the positions 12 and 13 with respect to the line X—X'. In this state, the amount of light incident to the detector 7 is measured. The value thus obtained is divided by the stored value. Thus, the influences of the reflectances of the plane mirror 9, the optical elements 10, 12 and the plane mirror 13 and eliminated to provide the reflectance of the sample 6.

The optical property measuring device according to this invention is constructed in the manner as mentioned above so that even if the sample, e.g. beam splitter prism is slightly inclined, the transmission light 17 or reflection light 18 can be necessarily focused in the neighborhood of the light receiving face 7a of the detector 7. This is because the light receiving face 7a of the detector 7 and the center 6a of the sample 6 are substantially in the conjugate relation for the second optical system.

Figure 2:
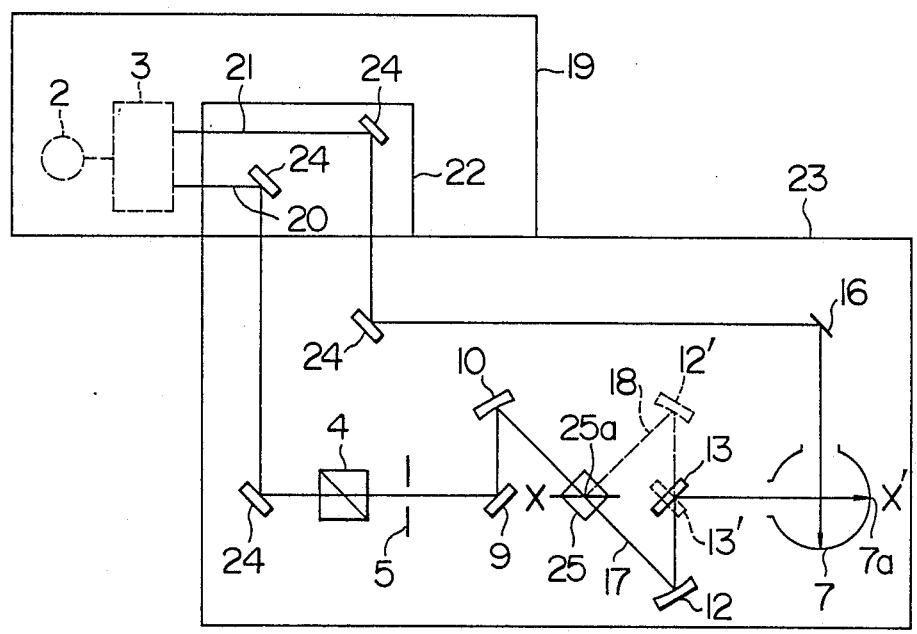
FIG. 2 shows an optical arrangement in which the optical property measuring device in accordance with one embodiment of this invention is implemented in an existing equipment.
Figure 3:
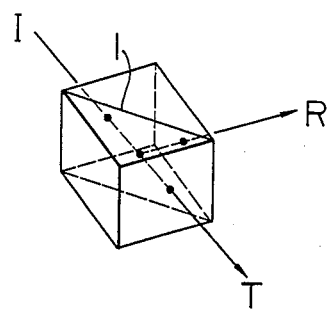
FIGS. 3 to 5 show perspective view of beam splitter prism which are used as samples to be measured.
Figure 4:
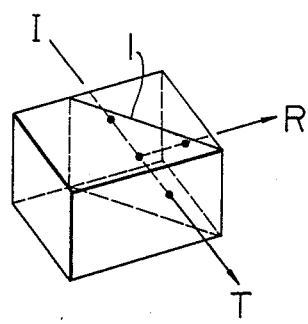
Figure 5:
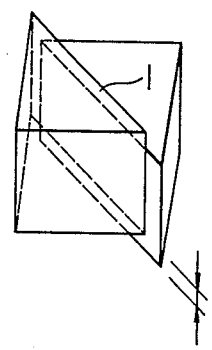
Figure 6:
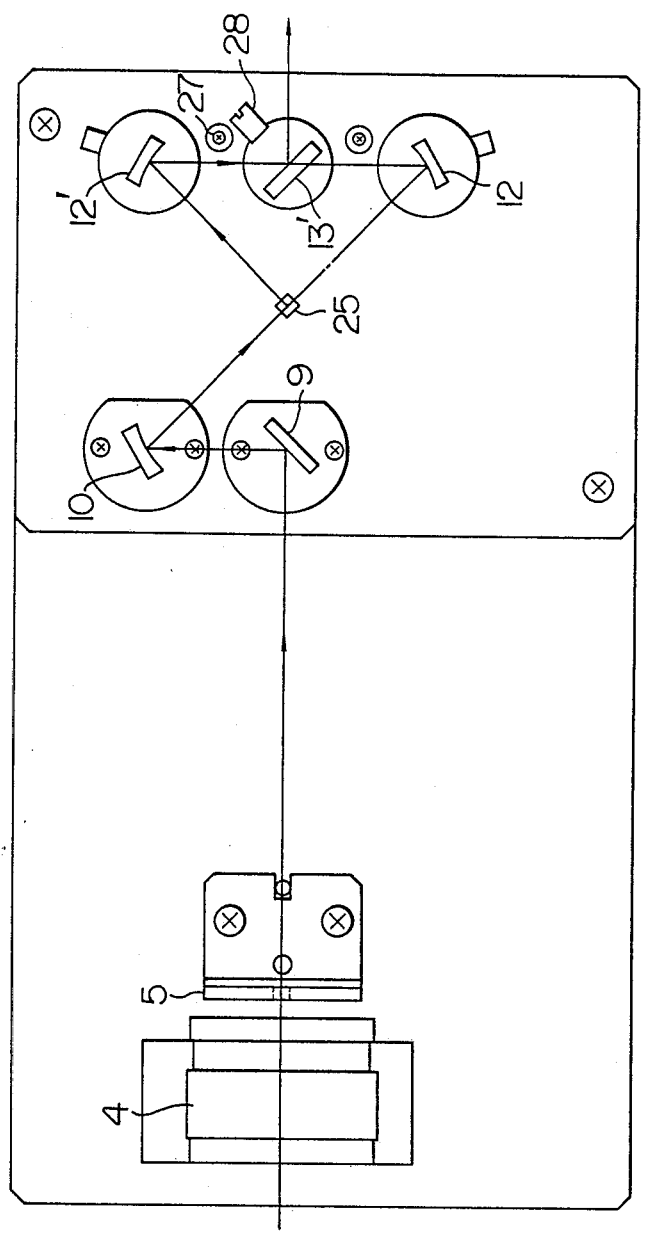
FIG. 6 is a plan view of the principal part of the optical property measuring device shown in FIG. 2.
Figure 7:
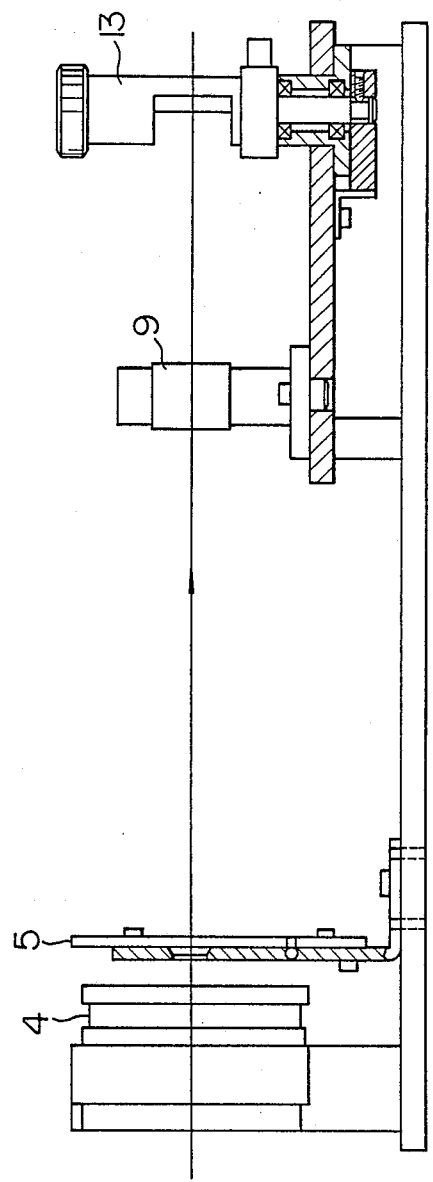
FIG. 7 is a front view of the principal part of the optical property measuring device shown in FIG. 2.
Figure 8:
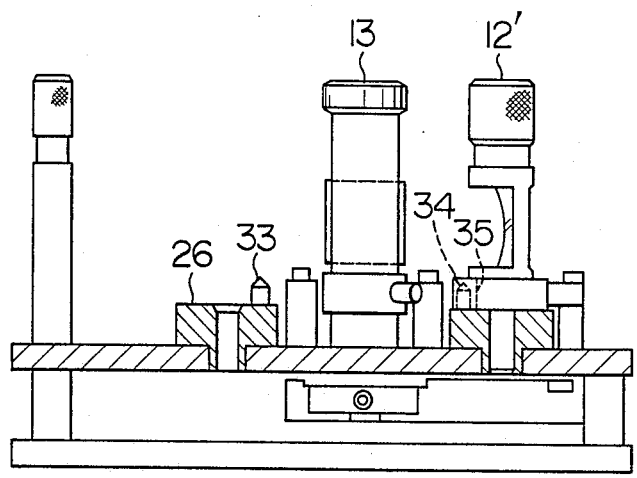
FIG. 8 is a right side view of the principal part of the optical property measuring device shown in FIG. 2.
Figure 9:
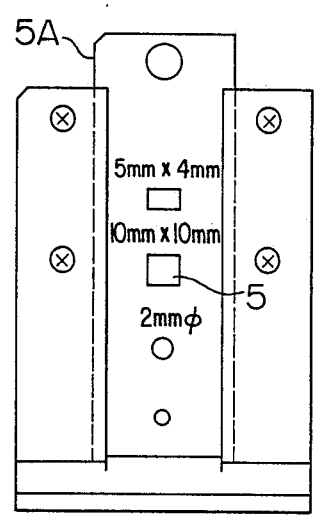
FIG. 9 is a front view of the diaphragm of the optical property measuring device shown in FIG. 2.
Figure 10:
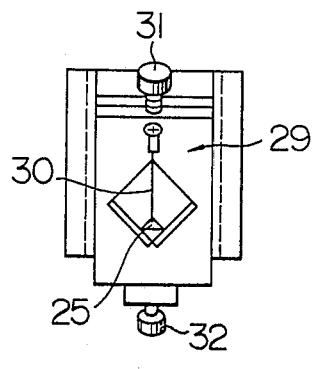
FIGS. 10 and 11 are a plan view and a side view of the sample holder in the optical property measuring device, respectively.
Figure 11:
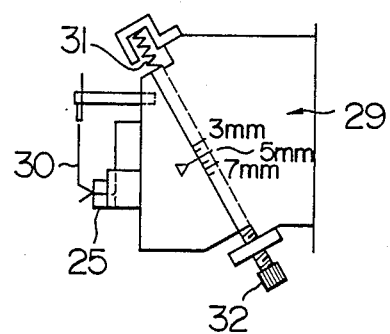

FIG. 2 shows an optical arrangement of the optical property measuring device which is composed of a spectrophotometer and a large-sized sample chamber integrating sphere which is externally arranged; FIG. 6 shows a plan view of the principal part of FIG. 2; FIG. 7 shows a front view thereof; FIG. 8 shows a right side view thereof; FIG. 9 shows a front view of the diaphragm shown in FIG. 2; and FIGS. 10 and 11 show a plan view and a side view of the sample holder shown in FIG. 2, respectively. In these figures, like reference numerals refer to like elements in FIGS. 1 and 3 to 5.

In these figures, 19 is a spectrophotometer which includes a spectroscope 3 that changes a light source 2 and white light into monochromatic light that is separated into reference light 21 and sample light 20. 22 is a sample chamber used for the measurement of e.g. solution. In this chamber, the reference light 21 and the sample light 20 are vertically bent by toroidal mirrors 24 so as to guided to the large-sized sample chamber 23. 25 is a sample to be measured which is e.g. a beam splitter prism such as shown in FIG. 5.

The diaphragm 5 includes plural openings provided in a diaphragm 5A as shown in FIG. 9; these opening having different shapes and sizes are adapted to be replaceable in accordance with the size of a sample 25. The diaphragm 5 is so arranged that the sample light 20 is focused, via the spherical mirror 10, substantially on the center 25a of the sample 25. The spherical mirror 12 is so arranged that a substantially conjugate relation exists between the center 25a of the sample 6 and the light receiving point 7a of the integrating sphere detector 7.

The spherical mirror 12 is provided with a guide 35 and pins 33, 34 as shown in FIG. 8 so that it can be shifted to the position 12' symmetrical thereto with respect to the line X—X'. FIG. 8 shows the spherical mirror shifted to the position 12' and a bearing guide 26 at the position 12.

The plane mirror 13 is adapted to be rotatable to the position 13' symmetrical thereto with respect to the line X—X'. 28 and 29 shown in FIG. 6 are pins and a stop, respectively which are provided for regulating the rotating angle.

The sample 25 is fixed by a sample holder generally designated as 29 as shown in FIGS. 10 and 11. More specifically, the sample 25 can be fixed by a sample holding-down member 30 and aligned by a spring 31 and a regulating screw 32. The details thereof are disclosed in Japanese U.M. Application No. 61-176,609.

Figure 12:
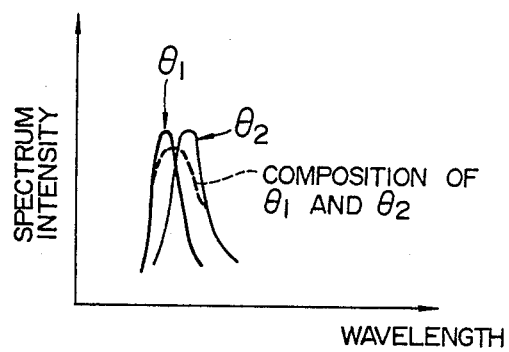
FIG. 12 is a graph showing the spectrum distribution of the sample.
Figure 13:
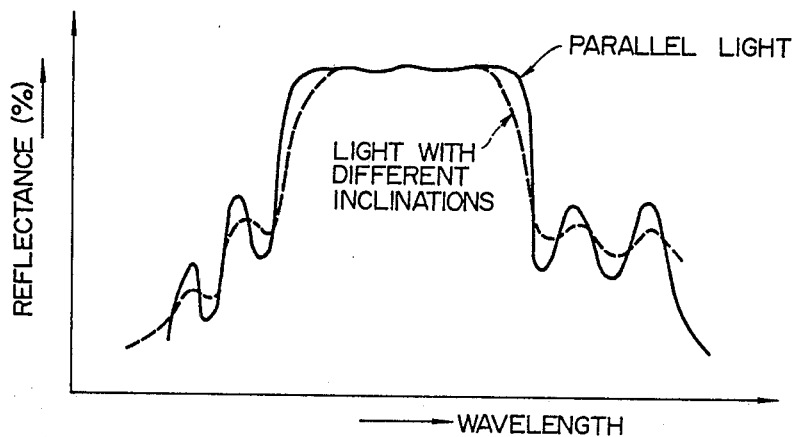
FIG. 13 is a graph showing the reflection characteristics of the sample.

It should be noted in the measurement of the transmittance or reflectance of the beam splitter prism that the monochromatic light flux irradiated to this sample is desired to be parallel light flux. If plural light rays with different irradiation angles (e.g. $\theta_1$, $\theta_2$) are mixed, an interference occurs among the light rays with different irradiation angles so that their respective interference wavelengths are slightly shifted and the composite spectrum thereof will be measured (see FIG. 12). Thus, the measured spectrum provides less sharpness than the parallel light flux (see FIG. 13). This is important when, in experimentally fabricating a sample, the number of deposition films is recognized from the reflecting spectrum mountain.

The light flux obtained from a common spectrophotometer has an inclination of up to 1° to 2°. When such a light flux is irradiated, an actual problem doesn't occur. However, when light is condensed by an optical component such as a lens or concave mirror in order to irradiate to a small-sized sample, it is necessary to calculate the angle of the irradiation light flux and thus provide parallel light (having an inclination of 1° to 1.6° or less) by limiting the light flux by e.g. a mask, as required.

The optical property measuring device according to this embodiment of the invention is constructed in the manner as mentioned above so that the sample 25 is set with an angle error of 1/50° or so, the image of the diaphragm 5 in the neighborhood of the sample 25 is focused on the light receiving point 7a of the integrating sphere detector 7 and thus reaches there without practically deviating from the normal optical path.

Thus, if the sample holder 29 holds the sample 25, e.g. beam splitter prism so that the center of the bonding face of the beam splitter prism is always located at a fixed position, the optical properties thereof can be measured. The direction of setting the beam splitter prism is not required to be so strict.

In this embodiment, the center of the sample and the light receiving point of the detector are in a conjugate relation for the second optical system so that even when the direction of setting the sample is slightly changed, the reflection light is surely projected on the light receiving portion.

Further, the image of the diaphragm is focused in the neighborhood of the center of the sample so that by varying the size of the opening of the diaphragm in accordance with the size of the sample, the diameter of the light flux at a measurement point and the measurement point thereof can be minutely adjusted.

Although in the embodiment, spherical mirrors have been used in the first and second optical systems, which can provide inexpensive optical systems, in place of them, ellipsoidal mirrors, toroidal mirrors and combinations of a lens and a plane mirror can be used. Further, in place of the integrating sphere detector used as a detector in the embodiment, a photo-electronic multiplier or a semiconductor detector can be used.

Moreover, the optical property measuring device which is capable of measuring both transmittance and reflectance of a sample has been explained in the embodiment. However, it is needless to say that on the same principle, the optical property measuring device dedicated to the measurement of the reflectance or transmittance of a sample can be provided.

This invention can provide an optical property measuring device which is capable of measuring the reflectance and transmittance of a sample such as a beam splitter prism and particularly measuring those of a small-sized beam splitter prism at good reproducibility, and so leads to great industrial effect.

We claim:

1. An optical property measuring device for measuring the optical properties of a sample by detecting the light irradiated thereto by a detector, comprising
    a first optical system arranged between a minute virtual light source for said light and said sample, said first optical system focusing the image of said minute virtual light source in the neighborhood of the measuring face of said sample; and
    a second optical system arranged between said sample and said detector, said second optical system having conjugate points in the neighborhood of the measuring point of said sample and of the light receiving portion of said detector.

2. An optical property measuring device according to claim 1, wherein said first optical system includes a refraction optical system and/or reflection optical system, and said second optical system includes a first and a second deflection optical system for changing the direction of said light.

3. An optical property measuring device according to claim 2, wherein said first and second deflection optical systems are adapted to be shiftable between the positions symmetrical with respect to the line connecting said sample and said detector.

4. An optical property measuring device according to claim 2, wherein said first deflection optical system is one selected from the group consisting of a spherical mirror, an ellipsoidal mirror, a toroidal mirror, and a combination of a lens and a plane mirror, and said detector is one selected from the group consisting of an integrating-sphere detector, a photoelectronic multiplier and a semiconductor detector.

5. An optical property measuring device according to claim 3, wherein said first deflection optical system is one selected from the group consisting of a spherical mirror, an ellipsoidal mirror, a toroidal mirror and a combination of a lens and a plane mirror, and said detector is one selected from the group consisting of an integrating-sphere detector, a photoelectronic multiplier and a semiconductor detector.

6. An optical property measuring device according to claim 1, further comprising a spectroscope and a polarizer, wherein said minute virtual light source is formed by monochromatic and linear-polarized light provided by said spectroscope and said polarizer, and a diaphragm.

7. An optical property measuring device according to claim 2, further comprising a spectroscope and a polarizer, wherein said minute virtual light source is formed by monochromatic and linear-polarized light provided by said spectroscope and said polarizer, and a diaphragm.

8. An optical property measuring device according to claim 3, further comprising a spectroscope and a polarizer, wherein said minute virtual light source is formed by monochromatic and linear-polarized light provided by said spectroscope and said polarizer, and diaphragm.

9. An optical property measuring device according to claim 1, wherein said sample is a beam splitter prism.

* * * * *